(12) United States Patent
Carter et al.

(10) Patent No.: US 7,031,144 B2
(45) Date of Patent: Apr. 18, 2006

(54) REVERSIBLE DISPLAY APPARATUS AND METHOD FOR APPLIANCES

(75) Inventors: David J. Carter, Asheville, NC (US); Walter J. Tipton, Asheville, NC (US)

(73) Assignee: GSLE Development Corporation, Charlotte, NC (US)

( * ) Notice: Subject to any disclaimer, the term of this patent is extended or adjusted under 35 U.S.C. 154(b) by 63 days.

(21) Appl. No.: 10/442,094

(22) Filed: May 21, 2003

(65) Prior Publication Data

US 2004/0114316 A1 Jun. 17, 2004

Related U.S. Application Data

(60) Provisional application No. 60/433,581, filed on Dec. 16, 2002.

(51) Int. Cl.
*G06F 1/16* (2006.01)
(52) U.S. Cl. .................... 361/681; 361/683; 361/680; 312/223.2; 312/405
(58) Field of Classification Search .............. None
See application file for complete search history.

(56) References Cited

U.S. PATENT DOCUMENTS

| | | | | |
|---|---|---|---|---|
| 4,814,759 A | * | 3/1989 | Gombrich et al. ............. 345/60 |
| 4,936,106 A | * | 6/1990 | Beach et al. .................. 62/131 |
| 5,145,137 A | * | 9/1992 | Choi ...................... 248/288.51 |
| 5,546,270 A | * | 8/1996 | Konno et al. ................ 361/680 |
| 5,862,468 A | * | 1/1999 | Kim ........................... 455/321 |
| 5,953,048 A | * | 9/1999 | Mikami et al. .......... 348/14.01 |
| 6,043,461 A | * | 3/2000 | Holling et al. ............ 219/445.1 |
| 6,098,411 A | * | 8/2000 | Jeon ............................. 62/125 |
| 6,359,270 B1 | * | 3/2002 | Bridson ...................... 219/679 |
| 6,445,385 B1 | * | 9/2002 | Shin et al. ................... 345/204 |
| 6,466,278 B1 | * | 10/2002 | Harrison et al. ............. 348/836 |
| 6,682,161 B1 | * | 1/2004 | Yun ............................. 312/405 |
| 6,692,093 B1 | * | 2/2004 | Park et al. ................ 312/405.1 |
| 6,719,383 B1 | * | 4/2004 | Elick et al. .................. 312/228 |
| 2002/0110489 A1 | * | 8/2002 | Reinhardt et al. ............. 422/64 |
| 2002/0180692 A1 | * | 12/2002 | Rhoads ........................ 345/156 |

FOREIGN PATENT DOCUMENTS

| DE | 3404256 A | * | 8/1985 |
|---|---|---|---|
| DE | 3520272 A | * | 12/1986 |
| JP | 02001215078 A | * | 8/2001 |
| JP | 02001324258 A | * | 11/2001 |
| JP | 02002178842 A | * | 6/2002 |
| KR | 2002056773 A | * | 7/2002 |
| KR | 370004 B | * | 8/2002 |

* cited by examiner

*Primary Examiner*—Michael Datskovskiy
(74) *Attorney, Agent, or Firm*—Baker & Hostetler LLP

(57) ABSTRACT

An apparatus and method for displaying interaction or an appliance, such as an incubator, provides a display module having a display face angled relative to the vertical plane. The display face can be angled upwardly or downwardly to face the line of sight of a user.

19 Claims, 5 Drawing Sheets

REVERSIBLE DISPLAY APPARATUS AND METHOD FOR APPLIANCES

PRIORITY

This application claims priority to the Provisional Patent Application Ser. No. 60/433,581 filed Dec. 16, 2002, entitled Reversible Display Bezel for Incubators and the Like, the disclosure of which is hereby incorporated by reference.

FIELD OF THE INVENTION

The present invention relates generally to the ergonomic design of a display for an appliance. More particularly, the present invention relates to the ergonomic design of an operational display and/or information display located on an appliance such as, for example, an environmental unit, and more particularly an incubator unit.

BACKGROUND OF THE INVENTION

Traditional appliances, including laboratory incubators, are known to typically have an operational and/or information display that is oriented in a plane that has a vertical face that is 90 degrees to the horizontal. Such an operational and information display may indicate information related to the appliance, such as for example the internal temperature of the atmosphere inside the unit. The display also may indicate operational mode settings, thermostat settings, or other information that is helpful in monitoring the condition of the unit, and/or that is used when inputting or confirming settings of the unit. The display may also be able to indicate malfunction of the unit.

Accordingly, it is desirable that the operational and information display be readily and easily visible to personnel in the vicinity of the unit. The substantially vertical orientation of conventional displays may be adequate where the display is located on a unit at an elevation relatively close to a horizontal line of sight for personnel in the vicinity. Because incubator units typically have a front door which occupies most of the front surface of the unit, it has been typical to provide the display near the top of the unit above the door. Thus, where units are approximately the height of a person, the vertically oriented display arrangement is satisfactory.

The displays typically may be a series of LED or LCD digital displays, generally having a transparent face plate in front of the LED or LCD elements. When the vertically oriented display has its face plate at an angle to the line of sight of the user, reflections can, often obscure the information being displayed, or at least make it difficult to read. Moreover, even without reflections the digits or characters on the display can become distorted and thus difficult to read when viewed from an angle. Therefore, when the display is located to high or too low above or below the user's visual line of sight, display effectiveness is comprised. This can occur for example in the case of a relatively short or relatively tall single incubator.

Another development which further causes conventional vertical displays to be undesirably located, either above or below the user's line of sight, is the increasing prevalence of stacked environmental units such as incubators. That is, it is becoming common for two medium sized units to be installed in a stacked configuration, thus providing greater flexibility than a single unit of the same height. In many conventional situations, this results in the lower unit having its display well below the line of sight of the personnel, and the upper unit having its display well above the person's line of sight. In either case, the viewer sees the display at an angle, often suffering from reflections and/or distortions.

In considering the problem of vertical display units having vertical faces being undesirably angled relative to the user's line of sight, another consideration is that it is desirable to control the cost and complexity of environmental units. In light of this consideration, it is desirable to keep components such as display components simple while providing desired functionality.

Accordingly, in view of the foregoing, there is a need in the art for a display method and apparatus for appliances, such as for example incubators, that can accommodate a difference in height between the height of the display and the line of sight of a user. Further, there is a need in the art for a single display element that can be adapted to be installed at more than one height, while still remaining oriented generally perpendicular to the user's line of sight.

SUMMARY OF THE INVENTION

The foregoing needs are met, to a great extent, by the present invention, which provides in some embodiments a display method and apparatus for appliances, such as for example incubators, that can accommodate a difference in height between the height of the display and the line of sight of a user. Further, some embodiments provide a single display element that can be adapted to be installed at more than one height, while still remaining oriented generally perpendicular to the user's line of sight, by virtue of being upwardly or downwardly angled.

In accordance with one embodiment of the present invention, an apparatus for displaying information related to an appliance comprises a display module having a display face that is selectively angled at least one of upwardly or downwardly relative to the vertical plane.

In accordance with another aspect of the present invention, a display apparatus for an appliance comprises means for displaying information related to the appliance, having a display face and means for supporting displaying means so that the display face is selectively angled at least one of upwardly or downwardly relative to vertical plane.

In accordance with yet another embodiment of the present invention, a method for displaying information related to an appliance includes providing a support structure mountable to the appliance; and orienting a display unit having a display face and adapted to be mounted to the support structure so that the display face is selectively angled at least one of upwardly or downwardly relative to vertical plane.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

The present invention provides an apparatus and method for displaying information on an appliance, for example a environmental unit such as an incubator. Preferred embodiments of the invention provide a display module having display surface when installed that is angled relative to the vertical plane. In some embodiments, the display module has bezel with a reversible vertical orientation so that the display surface angle can be selected between angled upwardly and angled downwardly.

Figure 1:
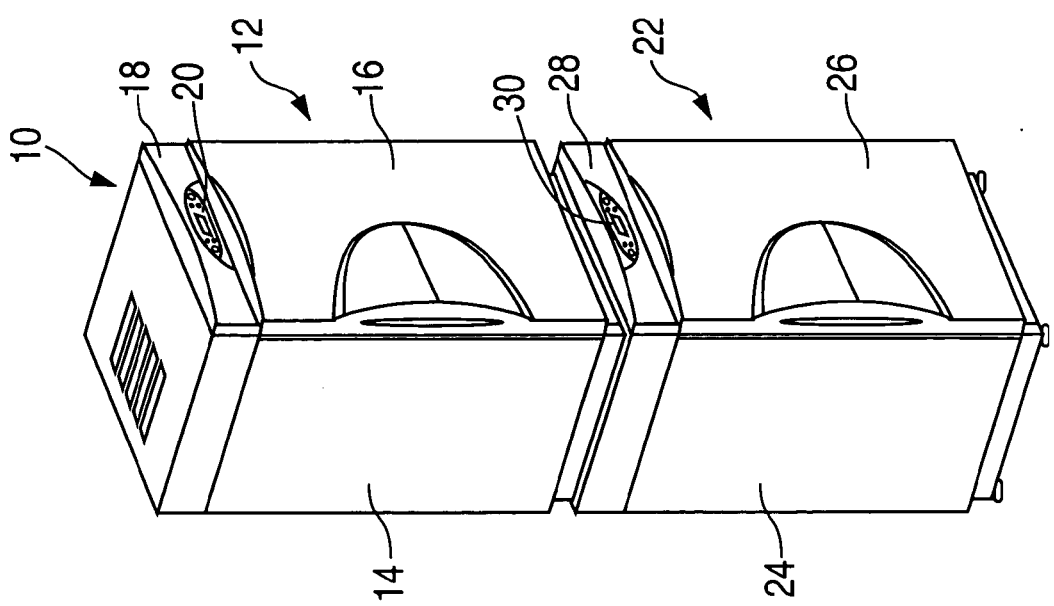
FIG. 1 is a perspective view of a preferred embodiment of a present invention used with two incubators in a stacked configuration.

Preferred embodiments of the invention will now described in reference to the drawing in which like reference numerals refer to like elements throughout. An embodiment of the present inventive apparatus and method is illustrated in FIG. 1, which is a perspective view showing a first incubator 12 stacked on top of a second incubator 22. The first incubator 12 includes a side housing 14 to which is mounted a hinged front door 16. An upper fascia 18 has a receptacle that receives a reversible angled display module 20.

Figure 3:
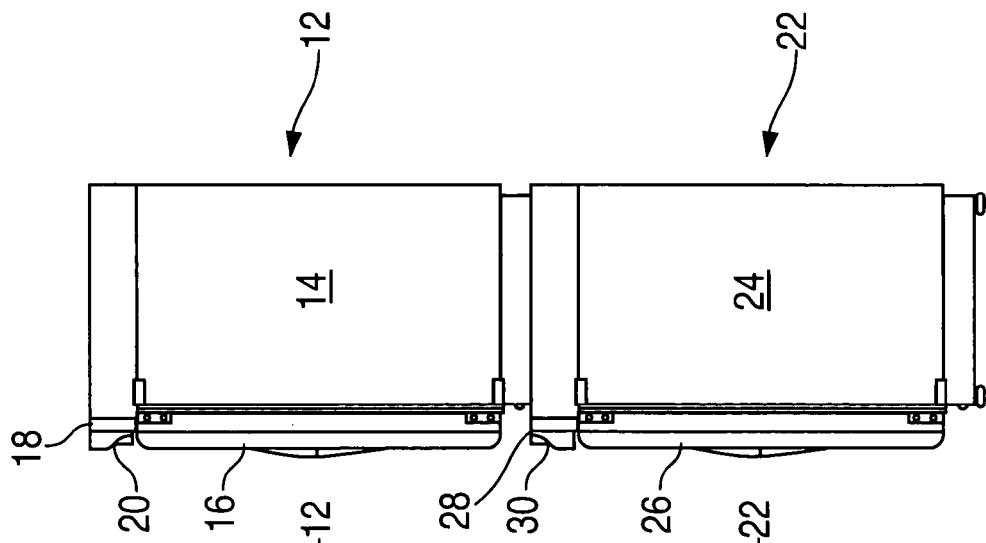
FIG. 3 is a side view of the arrangement of FIG. 1.
Figure 2:
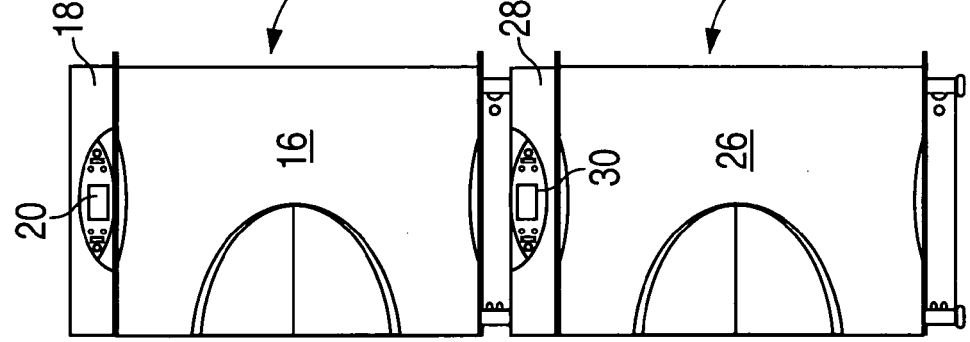
FIG. 2 is a front view of the arrangement of FIG. 1.

The incubator 12 is stacked on the second incubator 22, which has a side housing 24 to which is hingedly mounted a door 26. A upper fascia 28 has a receptacle for receiving a reversible angled display module 30. FIGS. 2 and 3 are front and side views respectively of the arrangement shown in FIG. 1.

The incubators 12 and 22 shown in FIGS. 1, 2, and 3 are substantially identical to each other, except for the orientation of the display modules 20 and 30. More specifically, the upper incubator unit 12 has its display module 20 oriented so that its face is angled downwardly, while the incubator unit 22 has its display module 30 with its face angled upwardly.

Figure 4:
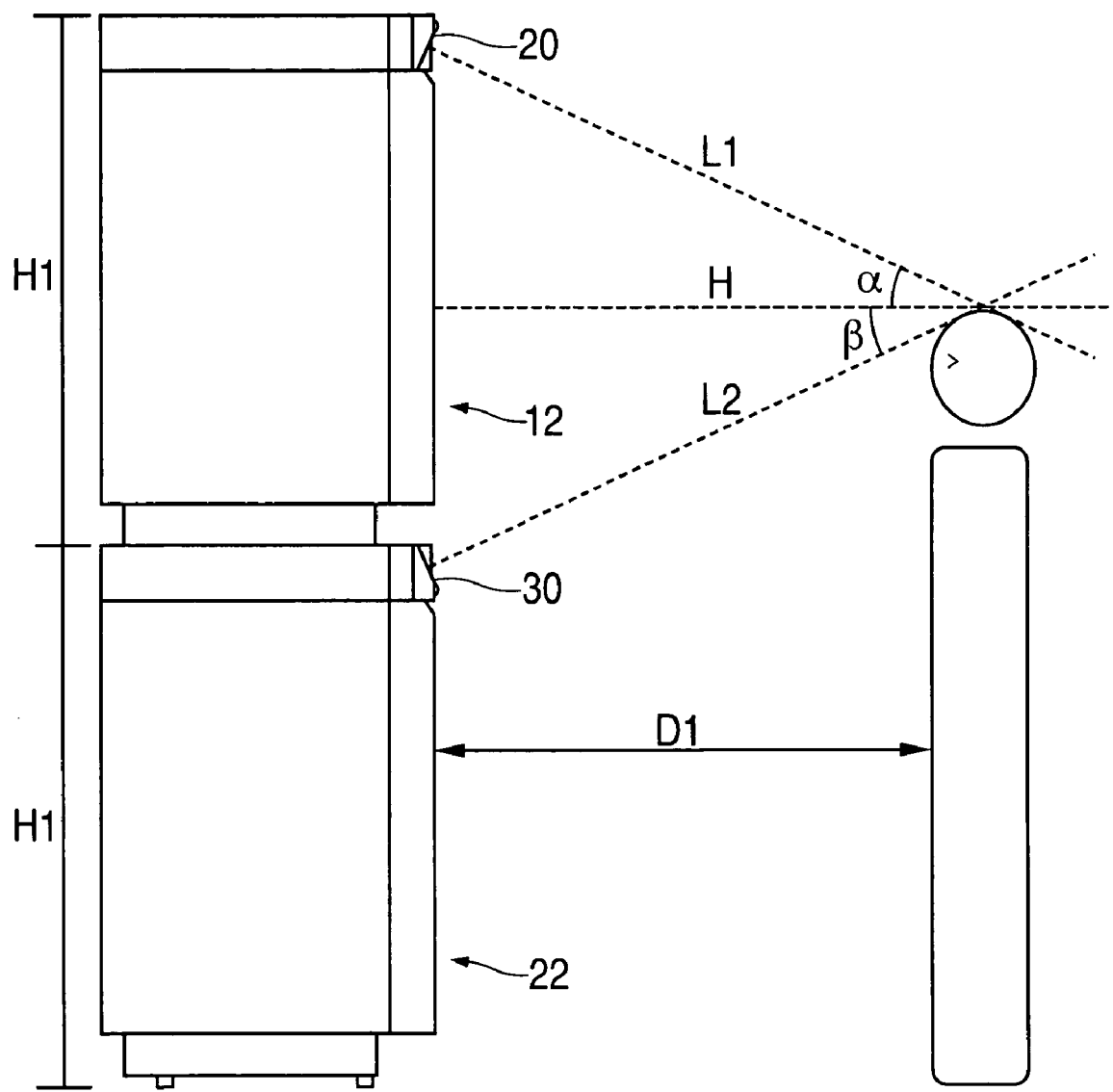
FIG. 4 is a schematic view of a preferred embodiment of the invention employed on a pair of stacked incubators.

The apparatus of FIG. 3 is shown schematically in the diagram of FIG. 4. In FIG. 4 it can be seen that the upper display module 20 has its display face angled downwardly with respect to vertical, while the display 30 has its face angled upwardly with respect to vertical. The angles with respect to vertical can be referred to as angles between the plane of the front face of the display and its associated LCD or LED elements, with respect to the vertical plane. FIG. 4 shows in dotted lines, lines L1 and L2, which are perpendicular to the plane of the first face and its associated LCD or LED elements, of the display units 20 and 30 respectively. The angle α indicates the line between L1 and an imaginary horizontal line H from the user's observation height. The angle β indicates an angle between the line L2 and the imaginary horizontal line H. In a preferred embodiment of the invention, it has been found that an angle α of 25 degrees and an angle of β also of 25 degrees are preferred in many typical commercial installations.

The preferred angles α and β of 25 degrees in this embodiment are selected based on typical size of incubators in industry as well as the typical distance a user tends to be positioned at when viewing the display units. For example, in FIG. 4 two relatively tall incubators are shown each having substantially the same height H1. In a typical example, the height H1 may be approximately 40 inches. If a user having their eyes approximately 5 feet above the ground views the incubators 12 and 22 from a typical standing distance D1 of 36 inches, then the 25 degree angles for α and β angles causes the user's eyes to be approximately on a perpendicular line of sight with the plane of the face of the displays 20 and 30. This provides a better view than if the displays 20 and 30 had a vertical face orientation, at which point the user would have a significant angle of view relative to the plane of the displays 20 and 30.

A significant advantage of some embodiments of the invention is that a single display module can serve as either upwardly angled display 20 and downwardly angled display 30 simply by reversing the vertical orientation of the module (or reversing a bezel of the module that holds a display module as described in more detail herein). Further, display modules can be manufactured having other angles and thus a given incubator can easily be retrofitted, to have its display 20 face either upwardly or downwardly, or at a different angle. In some embodiments, a single module can be flipped over to accommodate either upward or downward angles. Additional modules having different design angles can also be provided and can be made interchangeable with each other. These angled modules can also be interchangeable with modules having vertical faces. The preferred angle of 25 degrees is an example of a preferred angle for the described dimensions and geometry, however, it will be apparent that other angles can be selected to meet the appropriate circumstances.

Figure 5:
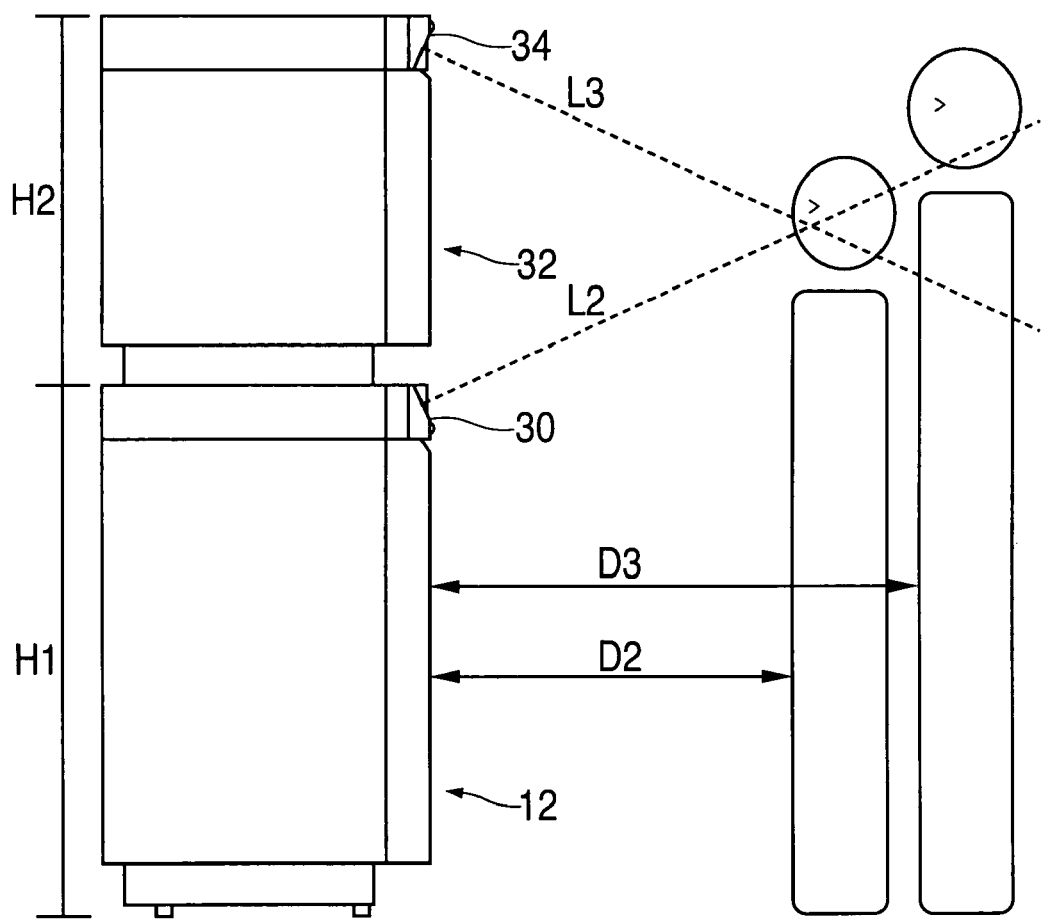
FIG. 5 is a schematic view of a preferred embodiment of the invention employed on another pair of stacked incubators.

Turning now to FIG. 5, a configuration is schematically illustrated where a first incubator 12 having a height H1 (the same as H1 in FIG. 4), has stacked thereon a second incubator 32 having a height H2 which is less than H1. In the illustrated example, the height H2 is approximately 28 inches. The line L2 is substantially the same in FIG. 5 as in FIG. 4 and thus a user five feet tall positioned a distance D2 of 28.5 inches has a substantially perpendicular line of sight to the plane of display 30. This user also has a relatively perpendicular line of sight the plane of display 34 as shown by line L3.

It will be appreciated that the users shown in FIGS. 4 and 5 do not necessarily have a perfectly perpendicular line of sight to the orientation of the display units 20, 30 and 34. However, the provision of some degree of angling in those circumstances certainly improves the line of sight compared to having a vertical display face orientation. In FIG. 5 the user located at D3 is shown taller than the user at D2, and is also further away from the incubators. It will be appreciated that as this occurs, the user located at D3 has a slightly less desirable line of sight compared to the user located at D2. Therefore, where the top unit of a stacked unit 32 is a relatively shorter unit, it may be preferable to use a display module 34 having a shallower angle less than 25 degrees.

Figure 6:
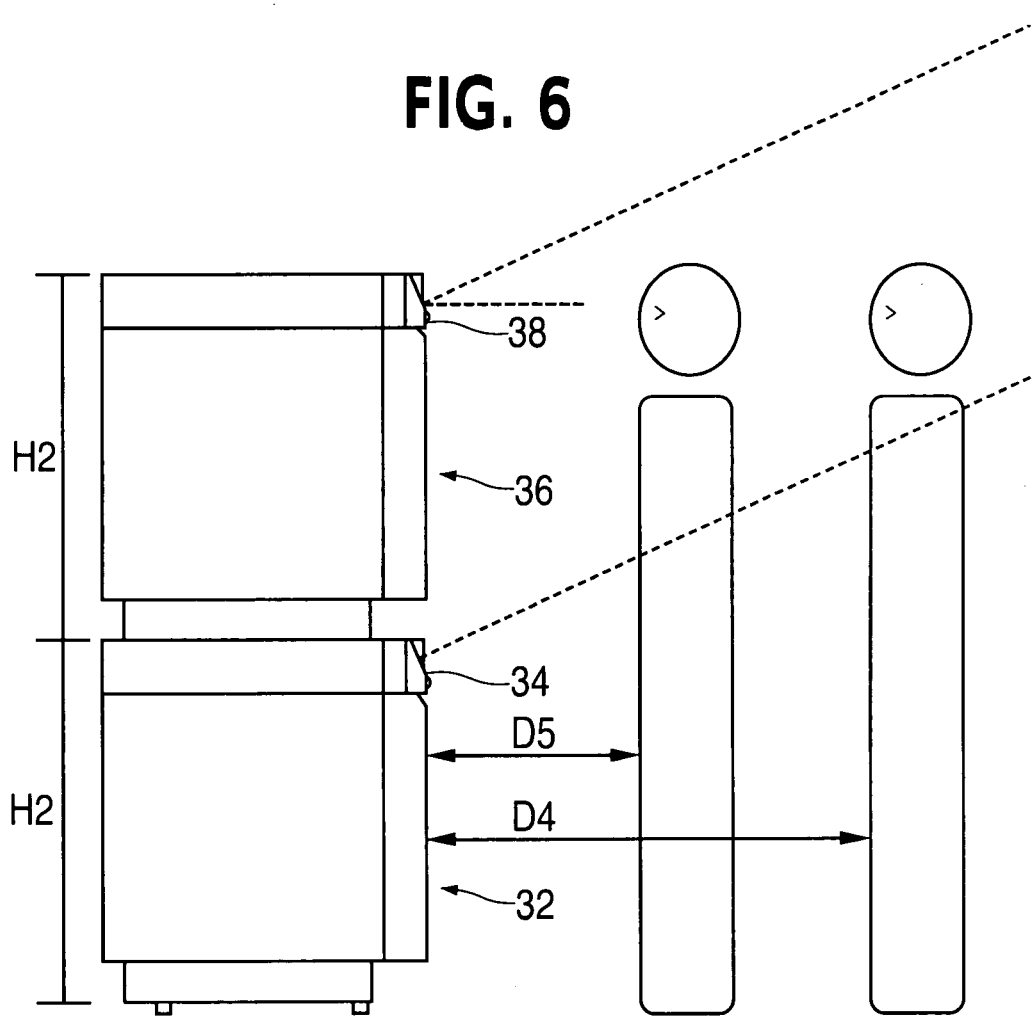
FIG. 6 is a schematic view of a preferred embodiment of the invention employed on another pair of stacked incubators.

FIG. 6 illustrates a configuration where two of the relatively shorter incubators 32 and 36 both having height H2 respectively are stacked onto of each other. In this configuration, it is beneficial for the lower display unit 34 to be angled upwardly as shown, regardless of whether the user is relatively far as shown in position D4 or relatively close as shown in position D5. However, in this configuration the top display unit 38 is at approximately eye level of the user, and thus it may be preferable in the configuration to use a vertically oriented display.

A benefit of the invention is that the front fascia 18, 28 of the incubators can be standardized for various sizes of incubators, and this standardized fascia can include a standardized socket for receiving a display module. Depending on the configuration of the incubators, and their distance from the user and the heights of users, it is possible to select either a vertically oriented or an angled display module, and to install the display in either an upward or downwardly angled condition. It is also possible to provide modules having different standardized angles and to select from these modules for a given incubator arrangement.

It will be appreciated that various embodiments of the invention provide for the condition where when the display is above the user, the display is angled downwardly and where the display is below the user the display is angled upwardly. This can be accomplished by a reversible display module 20.

Figure 7:
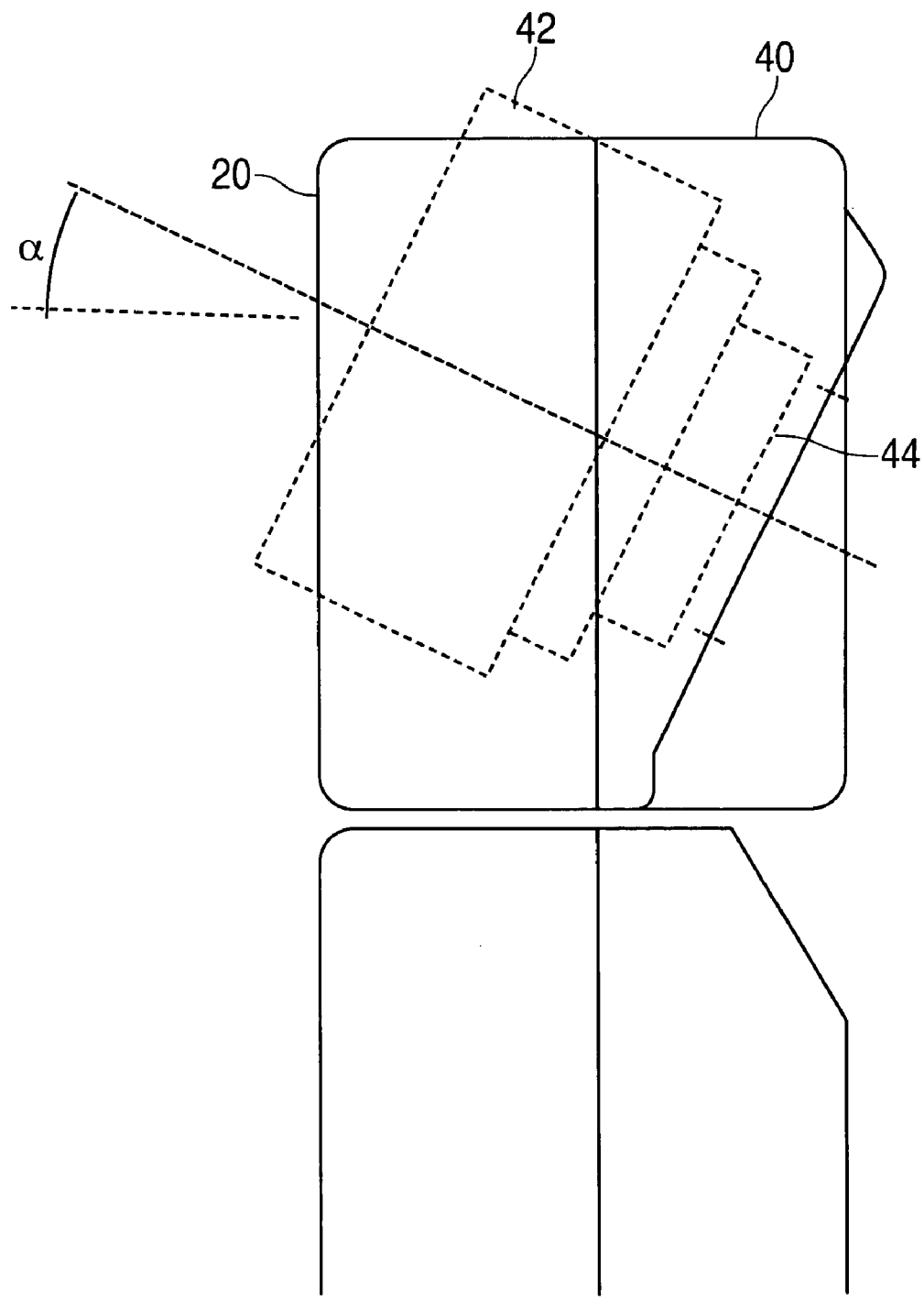
FIG. 7 is a layout view of a module having a reversible bezel according to a preferred embodiment of the present invention.

FIG. 7 schematically shows a preferred reversible angled display module 20. The module 20 has a reversible support bezel 40 which slides into a complimentary receptacle in the fascia 18. The module 20 further includes a display element 42 having a front display surface 44. The support bezel 40 serves as the mount for the display element 42, so that the display element 42 is upwardly or downwardly angled.

The different orientations are preferably achieved by the bezel 40 being reversible at installation and/or in the field. Preferably, the bezel 40 can be inserted into the receptacle of the fascia 18 in either of two orientations, each upside-down relative to the other orientation. Regardless of bezel orientation, the display element 42 can be supported upright by the bezel 40. Depending on the orientation of the bezel 40, the display element 42 will have its face 44 angled either upwardly or downwardly. The display elements 42 and bezel 40 together form a display module 20.

In a preferred arrangement, the display bezel 40 is a reversible component, and the actual display element 42 is removable and reinsertable into the bezel 40. Thus, it is only the bezel 40 that is flipped over to change from upward to downward angle. The actual LCD and LED display elements and associated wiring of the display 42 remain upright in either installation. However, in situations using for example an eight segment bar numeric display, or a dot matrix alpha numeric display, it is also possible to have a bezel with the display element permanently mounted therein so that the entire module including bezel and display element is completely flipped over. Such embodiments employ electronics to rotate the information displayed according to the actual orientation of the display.

By virtue of these features, in some embodiments the orientation of the display unit can be initially selected during the installation at the factory, but can be changed at any time by the user, either during installation, or upon a reinstallation in another location or configuration. Thus, some embodiments of the invention provide a flexible ergonomic interface that is user friendly and better suited to addressing many individual and user requirements as compared to the fixed vertical face displays in previous use.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An apparatus for displaying information related to an appliance, comprising:
    a display element having a display face configured to be selectively angled at least one of upwardly or downwardly relative to a vertical plane;
    a reversible bezel mounted to the appliance and configured to be attached to the appliance in two opposite orientations, comprising a first orientation corresponding to the display face being angled upwardly relative to the vertical plane, and a second orientation corresponding to the display face being angled downwardly relative to the vertical plane.

2. The apparatus of claim 1, wherein the second orientation is inverted with respect to the first orientation.

3. The apparatus according to claim 1, wherein when mounted the display face has an angle of approximately 25 degrees relative to the vertical plane.

4. The apparatus of claim 1, wherein the display element is removably mountable in the bezel.

5. The apparatus of claim 4, wherein the bezel in each of the first and second orientations supports the display element in the same upright position, with the display face having one of an upward angle or downward angle depending on the bezel orientation.

6. The apparatus of claim 1, wherein the display element displays information related to at least one of an operating condition and an operating mode of the appliance.

7. The apparatus of claim 1, wherein the appliance is an incubator.

8. A display apparatus for an appliance, comprising:
    means for displaying information related to the appliance, having a display face;
    means for supporting the displaying means to have the display face selectively angled at least one of upwardly or downwardly relative to a vertical plane; and
    means for attaching a bezel to the appliance in two opposite orientations, comprising a first orientation corresponding to the display face being angled upwardly relative to the vertical plane, and a second orientation corresponding to the display face being angled downwardly relative to the vertical plane.

9. The apparatus of claim 8, wherein the supporting means is a reversible bezel reversibly mountable to the appliance.

10. The apparatus of claim 8, wherein when mounted the display face has an angle of approximately 25 degrees relative to the vertical plane.

11. The apparatus of claim 8, wherein the displaying means is removably mountable in the bezel.

12. The apparatus of claim 11, wherein the bezel in each of the first and second orientations supports the displaying means in the same upright position, with one of upward angle or downward angle depending on the bezel orientation.

13. The apparatus of claim 8, wherein the displaying means displays information related to at least one of an operating condition and an operating mode of the appliance.

14. The apparatus of claim 8, wherein the appliance is an incubator.

15. The apparatus of claim 8, wherein the second orientation is inverted with respect to the first orientation.

16. The method of claim 14, wherein the display element is supported such that the display face has an angle of approximately 25 degrees relative to the vertical plane.

17. A method of displaying information related to an appliance, comprising:

supporting a display element such that a display face is selectively angled at least one of upwardly or downwardly relative to a vertical plane;

attaching a bezel to the appliance in one of two opposite orientations, comprising a first orientation corresponding to the display face being angled upwardly relative to the vertical plane, and a second orientation corresponding to the display face being angled downwardly relative to the vertical plane; and displaying information related to the appliance on the display face.

18. The method of claim 17, wherein the appliance is an incubator.

19. The method of claim 17, wherein the second orientation is inverted with respect to the first orientation.

* * * * *